United States Patent

Bains, Jr.

[11] Patent Number: 4,620,152
[45] Date of Patent: Oct. 28, 1986

[54] LIFT-OFF COMPENSATION OF EDDY CURRENT PROBES BY TRANSLATING WITHOUT ROTATION THE X-Y COORDINATE PLOT OF THE COMPLEX LOCUS OF THE PROBE OUTPUT

[75] Inventor: James A. Bains, Jr., Pearland, Tex.

[73] Assignee: AMF Tuboscope, Inc., Houston, Tex.

[21] Appl. No.: 457,321

[22] Filed: Jan. 11, 1983

[51] Int. Cl.$^4$ ............... G01N 27/72; G01R 33/12
[52] U.S. Cl. .................................. 324/225; 324/233
[58] Field of Search ......... 324/225, 233, 202, 239–243

[56] References Cited

U.S. PATENT DOCUMENTS

| | | | |
|---|---|---|---|
| 2,980,849 | 4/1969 | Datt et al. | 324/225 |
| 3,197,693 | 7/1965 | Libby | 324/225 |
| 3,358,225 | 12/1967 | Peugeot | 324/225 |
| 3,496,458 | 2/1970 | Bromley | 324/225 |
| 4,322,683 | 3/1982 | Vieira et al. | 324/233 |

Primary Examiner—Ernest F. Karlsen
Assistant Examiner—Walter E. Snow
Attorney, Agent, or Firm—Finnegan, Henderson, Farabow, Garrett & Dunner

[57] ABSTRACT

This invention relates to a method and apparatus for compensating the output signal of a reflection type eddy current probe so as to minimize the change in the phase shift of the probe output signal that otherwise would occur as a result of a change in the spacing of the probe from the surface of the metal sample being inspected or investigated.

7 Claims, 7 Drawing Figures

LIFT-OFF COMPENSATION OF EDDY CURRENT PROBES BY TRANSLATING WITHOUT ROTATION THE X-Y COORDINATE PLOT OF THE COMPLEX LOCUS OF THE PROBE OUTPUT

BACKGROUND OF THE INVENTION

In the commercial nondestructive inspection of metallic tubular goods by the conventional eddy current method, an excited eddy current probe comprised of one or more input or primary windings and one or more output or secondary windings is passed along the surface of the tubular member being inspected. The output signal from the eddy current probe is monitored to determine a change in the phase angle of the probe output signal. Such a change provides an indication of an anomaly in the wall of the pipe or a change in the wall thickness of the pipe. In practice, the windings of the probe are spaced from the surface of the tubular member by some slight distance. Either or both the probe and the tubular member are moving and, as a practical matter, it is virtually impossible to prevent the spacing between the windings and the surface of the tubular member from changing. This changing separation is known as lift-off and causes the output signal from the probe to change in both magnitude and phase. It has long been a major effort in the art of eddy current inspection to provide effective methods and apparatus for eliminating the effect of probe lift-off from the eddy current inspection signals.

I have been able to achieve the above objective by the use of relatively simple, inexpensive, and reliable means that is easy to use and readily adapted for commercial operations.

BRIEF DESCRIPTION OF DRAWINGS

The present invention will be described by referring to the accompanying drawings wherein.

DETAILED DESCRIPTION OF PREFERRED EMBODIMENT

Figure 1:
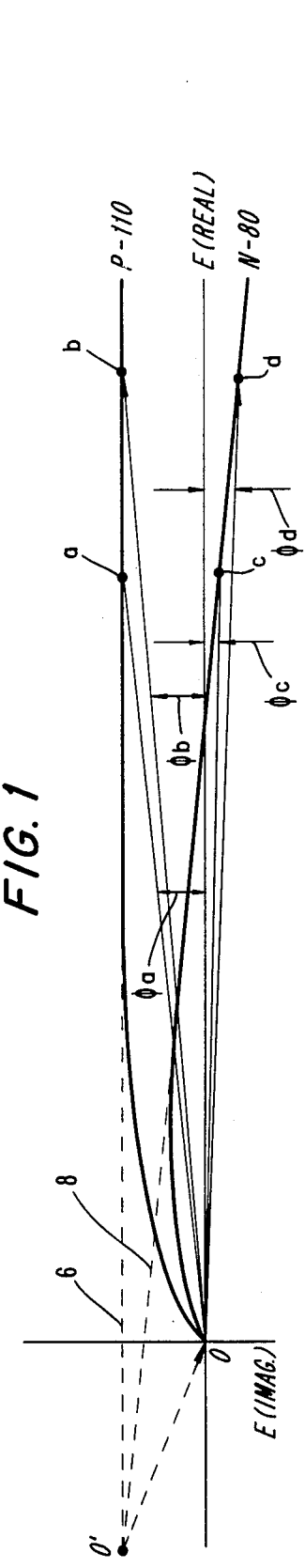
FIG. 1 illustrates respective plots, in rectangular coordinates, of the complex loci of output signals from an eddy current probe whose lift-off is varied from the surfaces of samples of different grade steels.

Reference first will be made to FIG. 1 to illustrate the well understood nature of the change in the output signal of the reflection type eddy current probe as a function of lift-off, or separation, of the probe from the surface of the metal sample being inspected. Each of the curves represents the complex locus of the eddy current probe output signal, as a function of lift-off, for respective samples of pipe made from different grades of steel, i.e., P-110 grade and N-80 grade. Other grades of steel will produce similar, noncoincident, curves so that many different grades will produce a family of curves, each of which begins on the left at the origin O and has a linear portion in the useful lift-off range. The portions of the curves at the origin represent the greatest lift-off distances. At these maximum lift-off distances the metal sample has substantially no observable influence on the probe impedance. The portions of the curves on the right represent the least distances of lift-off of the probe from the surfaces of the samples. Looking at the curve for the grade of steel P-110, for example, the point "a" corresponds to one lift-off distance and the point "b" represents a different and smaller lift-off distance. It is seen that the phasors O-a and O-b, which correspond to the probe output voltages at the lift-off distances "a" and "b", are different in magnitude and phase. The phasors O-c and O-d to the points "c" and "d" on the curve for the sample of N-80 grade steel show similar characteristics of magnitude and phase variations for different lift-off distances. Since it is the phase of the probe output signal that is monitored to provide an indication of an anomaly or wall thickness in the inspected sample, the illustrated changes in the phase angles associated with a respective curve will lead to erroneous or confusing inspection signals.

It is noted that the curves of FIG. 1 approach linearity at respective angles relative to the coordinate axes. By extending the substantially linear portions of the curves toward the left by means of the broken lines 6, 8 in FIG. 1, the extentions will intersect at the point O'. The extentions of the substantially linear portions of the curves for other grades of steel also will intersect at the point O'.

Figure 2:
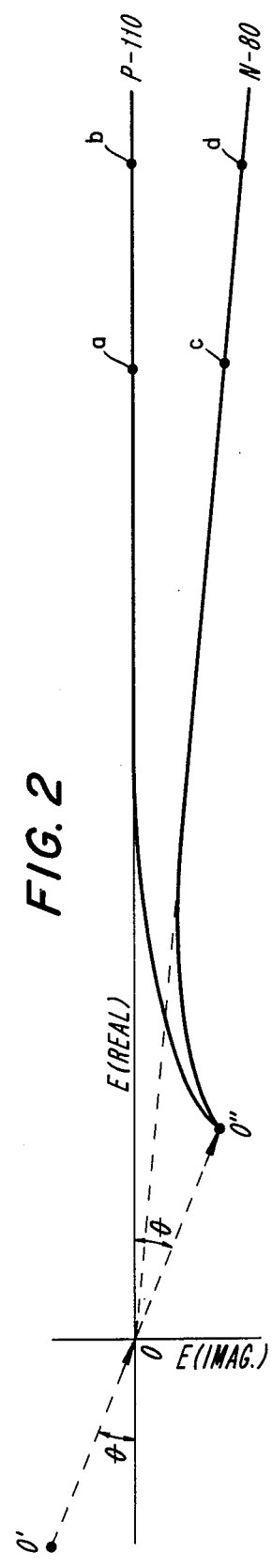
FIG. 2 illustrates the plots of FIG. 1 translated from their positions in FIG. 1 in accordance with the teachings of this invention, and also shows some construction lines that are used in explaining the principles of the invention.

The concept of the compensation method that I employ in my present invention to minimize (ideally to eliminate) the change of phase angle as a function of lift-off for a given sample of metal is illustrated in FIG. 2. In effect, I add the phasor O'-O to the origin O and to every point on the two curves. This translates the origin O to the point O'', and translates the P-110 and N-80 curves in like manner to the positions illustrated in FIG. 2. Stated differently, the new origin O'' of the curves is on a straight line extention through the origin from the intersection point O', and at the same distance from the origin as the intersection point O'. It will be seen in FIG. 1 that a phasor O-a from the origin O to the lift-off point "a" on the P-110 curve, and a phasor O-b from the origin to lift-off point "b" are at substantially the same phase angle. This condition is true for the entire length of the substantially linear portion of the curve for P-110 grade steel. Similarly, a phasor O-c from the origin O to lift-off point "c" is at substantially the same phase angle as the phasor O-d to lift-off point d on the curve of N-80 grade steel. The linear portions of the curves of FIGS. 1 and 2 represent the operating regions in practice. Accordingly, the phase angle of the probe output signal will be substantially constant so that inspection signals are obtained which are substantially free of lift-off influence. It is to be noted that the phase angle associated with each curve of a family of curves in FIG. 2 will be different. Since the amplitude of the probe output signal is not used to detect anomalies in the sample, its change in magnitude is of no concern.

It also will be noted that the translation of the P-110 and N-80 curves from their positions in FIG. 1 to their positions in FIG. 2 is without rotation of the curves about the origin O.

Figure 3:
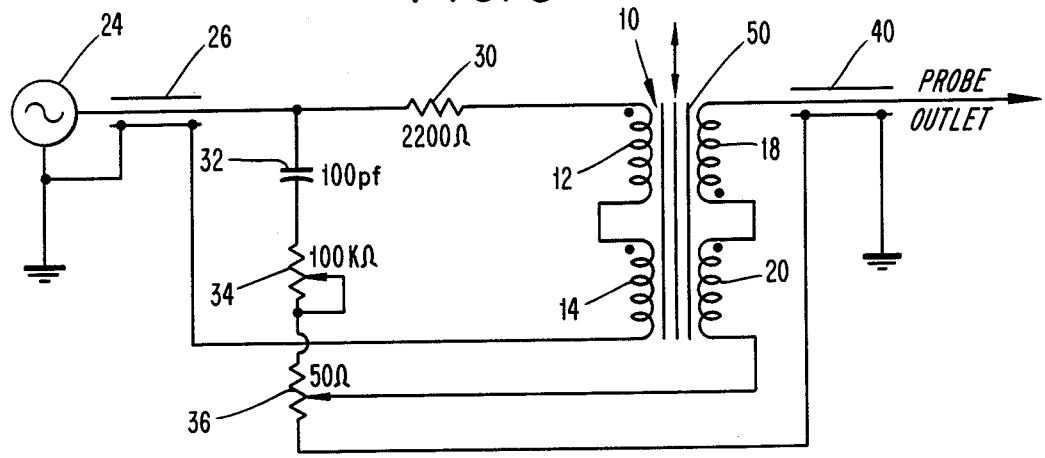
FIG. 3 is a simplified schematic diagram of an eddy current probe and a presently preferred compensation means.

I have determined that there are a variety of means by which I can, in effect, translate the points on the plots of the complex loci of the output signals of the eddy current probe. Basically, my method is comprised of adding to the probe output signal a compensating signal of like frequency whose amplitude and phase correspond to the phasor O'-O of FIG. 1. A presently preferred embodiment of my invention is illustrated in FIG. 3 wherein the input or primary winding of the probe 10 is comprised of a pair of like coils 12 and 14, and the output or secondary winding is comprised of coils 18 and 20 connected in series opposed relationship. In one embodiment of my invention, each of the four coils of the probe is comprised of 150 turns of number 36 wire. A source 24 of exciting current at 10 kHz, for example, is coupled through a section of coaxial cable 26 and a resistor 30 to input coils 12 and 14. The bottom end of coil 14 is grounded to the ground conductor of coaxial cable 26.

A compensating circuit comprised of capacitor 32, potentiometer 34 and potentiometer 36 is coupled to source 24 at the input side of resistor 30. The slider of potentiometer 36 is coupled to the bottom terminal of output coil 20, and the top terminal of output coil 18 is coupled through coaxial cable 40 to the probe output terminal. The bottom terminal of potentiometer 36 is coupled to ground through the ground conductor of coaxial cable 40. A ferromagnetic core or slug 50 is included within eddy current probe 10 and is adjustable in position so as to make the balance of the probe adjustable. In practice, the transformer windings are wound on a two section bobbin with coil 18 wound within coil 12 in one section and with coil 20 wound within coil 14 in the other section. Ferromagnetic core 50 is disposed axially within the bobbin in threaded engagement therewith so as to provide means for translating the core within the bobbin.

Figure 6:
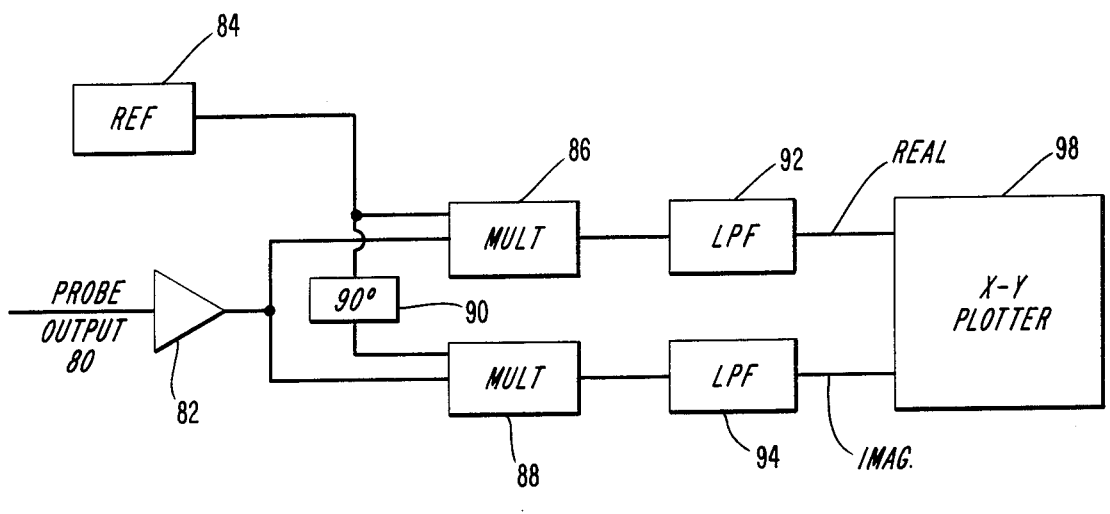
FIG. 6 is a simplified block diagram that is used to explain how the plots of FIGS. 1, 2 and 4 are made.

The method of compensating the probe 10 of FIG. 3 in accordance with this invention is as follows. The eddy current probe output signal is coupled to the apparatus illustrated in FIG. 6 so that the X-Y plotter will plot the complex locus of the probe output signal. FIG. 6 will be explained in detail below. The slider of potentiometer 36 is turned to its bottommost position so that the potentiometer effectively is out of the circuit. Potentiometer 34 is adjusted so that its slider is at one extreme position, its uppermost position, for example. The probe is withdrawn from the surface of the sample being inspected so that its impedance is substantially free of influence from the sample, and from any other metallic object. At this time the pen of the X-Y plotter likely may be at a location other than the origin O. The ferromagnetic slug 50 of the probe is adjusted until the pen of the X-Y plotter moves to the origin O of the coordinate system. In practice, the probe then would be "potted", i.e., molded in a plastic material with only its leads exposed. The position of the probe then is varied from one position in contact with the test sample to an opposite extreme position that is out of the field of influence of the sample. As the probe is moved, the changing output signal is plotted to produce the P-110 curve of FIG. 1, for example.

With the plotted probe, the above procedure then is repeated with one or more samples of different grades of steel so that a family of curves of the type illustrated in FIG. 1 is plotted. Extentions of the linear portions of the curves than are drawn by hand toward the left of the curves to locate the intersection point O'. A line then is drawn from the point O' through and beyond the origin a distance equal to O'-O so as to locate the point O" of FIG. 2. With the probe removed from the influence of the sample and from other metallic objects, potentiometers 34 and 36 of FIG. 3 are empirically adjusted until the X-Y plotter moves its pen to the point O" of FIG. 2. The compensation then is complete and the probe may be used for the inspection of any of the grades of steel involved in the plot of FIG. 2 with the assurance that the phase angle of the output signal will not substantially vary as a function of lift-off. As mentioned above, the respective phase angles for the various grades of steel may be different from each other, but those respective values will not substantially change as a function of lift-off.

Figure 5:
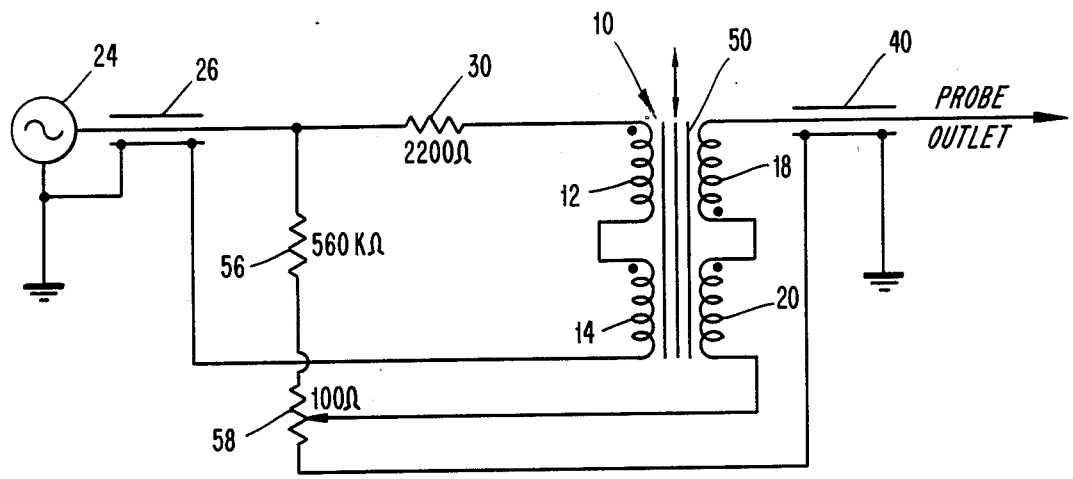
FIG. 5 is a simplified schematic diagram of a different embodiment of my invention.

FIG. 5 illustrates a compensating circuit similar to that of FIG. 3 except that it has no capacitor and only one potentiometer 58. A fixed resistor 56 replaces potentiometer 34 of FIG. 3. Compensating the probe output signal with the circuit of FIG. 5 is similar to the procedure explained above for the circuit of FIG. 3. The primary difference in compensating with the circuit of FIG. 5 is that the ferromagnetic core 50 is used as one compensating means, along with potentiometer 58, to provide a compensating voltage. As explained above, this voltage corresponds to phasor O'-O and is added to the induced voltage in secondary coils 12 and 14. Accordingly, slug 50 must be available for adjustment after the probe is potted.

Figure 4:
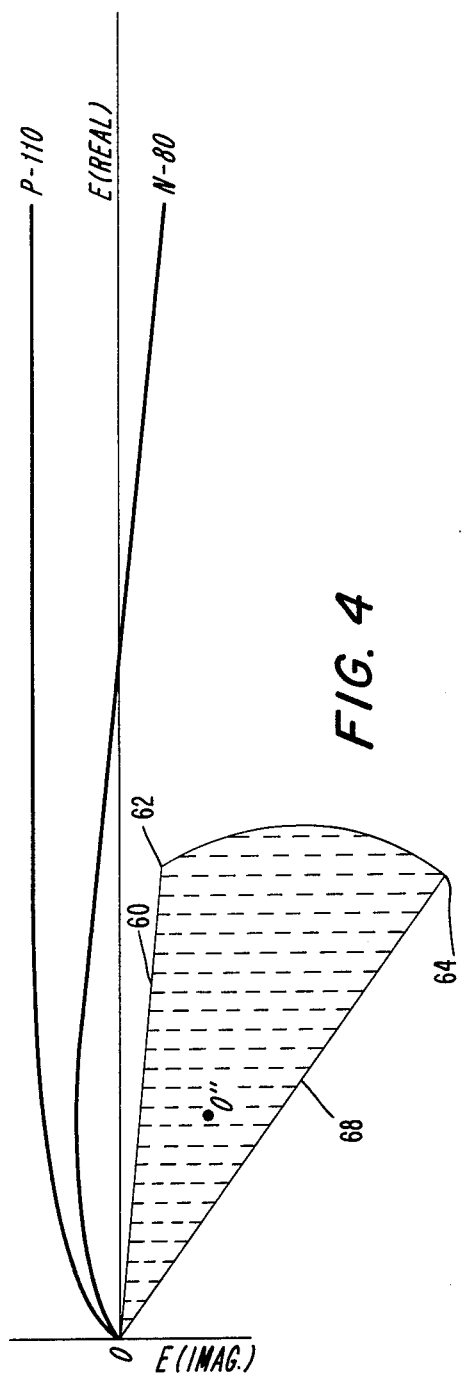
FIG. 4 shows the plots of FIG. 1 and the region within which the origin of the curves may be translated in one embodiment of this invention.

FIG. 4 is an illustration of the range of compensation that may be achieved with the embodiment of the invention illustrated in FIG. 3. For example, with the sliders of potentiometers 34 and 36 turned to their bottommost positions, and with the probe removed from the influence of metallic objects, the ferromagnetic slug 50 is adjusted until the X-Y plotter pen is at the origin O of the coordinate system. As the potentiometer 36 is turned to increase its resistance value the plotter moves from the origin along the straight line 60 to the point 62. Potentiometer 34 then is turned to decrease its resistance to it minimum value. This causes the plotter to draw the curve from point 62 to point 64. Potentiometer 36 then is turned to move its slider to the lowest position which effectively removes its resistance from the circuit. This causes the plotter pen to move from point 64 along the straight line 68 back to the origin. With the range of variation of circuit parameter values illustrated in FIG. 3, the point O" can be moved anywhere within the shaded region of FIG. 4. The shape of this shaded region can be changed by changing the parameter values in the circuit of FIG. 3.

Apparatus that may be used to plot the curves of FIGS. 1, 2 and 4 according to the method described above is illustrated in simplified block form in FIG. 6. The output signal from the eddy current probe of FIG. 3 or 5, for example, is coupled as an input on lead 80 and is amplified and filtered in amplifier and filter means 82. The output signal of amplifier 82 is coupled as one input to each of the multiplier or mixer circuits 86 and 88. A reference signal from reference source 84 at the same frequency as the exciting signal from probe 10 of FIG. 3 is coupled as a second input to multiplier 82, and after passing through 90° phase shifter 90, is coupled as the second input to multiplier 88. All but the lowest frequency components are filtered from the respective output signals of the multipliers by low pass filters 92 and 94. Multipliers or mixers 86, 88 and filters 92, 94 function as phase-sensitive detectors and produce respective DC output signals that are proportional to the amplitude of the component of the eddy current signal which is in phase with the respective reference component input to that detector. The outputs of the filters comprise the real and imaginary components of the eddy current signal. These signals are coupled as inputs to X-Y plotter 98 which plots the curves of FIGS. 1, 2 and 4.

All of the apparatus of FIG. 6 except X-Y plotter 98 is provided in a piece of test equipment known as a "Lock-In Analyzer", model 5204, manufactured by Princeton Applied Research Corporation, Princeton, N.J. Any suitable type of commercially available X-Y plotter may be employed in the arrangement of FIG. 6.

The compensation circuits illustrated in FIGS. 3 and 5 use solely passive components and are particularly attractive for that reason. An embodiment of the invention that uses an active component as illustrated in the simplified schematic diagram of FIG. 7. Source 102 that corresponds to source 24 in FIGS. 3 and 5 is coupled through fixed resistor 108 to the primary winding 112 of the eddy current probe 110. The bottom of primary winding 112 is grounded. A secondary winding comprised of a pair of series opposed coils 114 and 116 are inductively coupled to the primary. The top terminal of coil 114 is connected through variable resistor R2 to the negative input of operational amplifier 126. The bottom terminal of secondary coil 116 is grounded, as is the positive input terminal of the amplifier. Feedback resistor R3 is coupled between the output terminal and the negative input terminal of amplifier 126.

Figure 7:
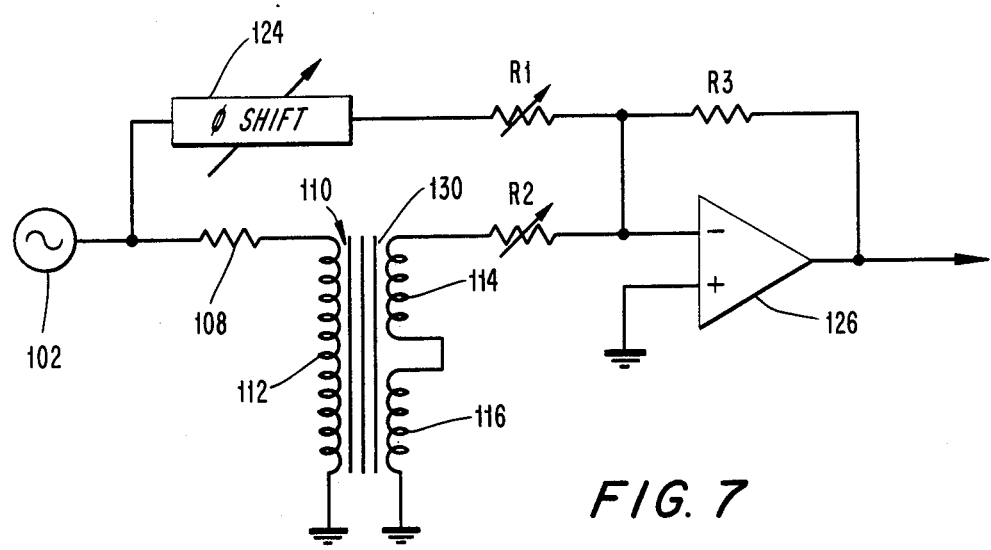
FIG. 7 is a simplified schematic diagram of another embodiment of this invention.

The compensation means of FIG. 7 includes a phase shift network 124 and a variable resistor R1 coupled from exciting source 102 to the negative input terminal of amplifier 126, i.e., the output of the secondary windings. Phase shift network 124 may be any known type of such circuit.

Using the general procedure explained above, the resistance values of variable resistor R2 and/or resistor R1 may be varied and the phase shift produced by phase shift network 124 may be varied to produce an empirically derived compensating voltage that substantially eliminates from the phase of the output signal of amplifier 126 any change due to lift-off. As in the above examples, this compensating voltage corresponds to the phasor O-O" in FIG. 2.

From the above description it is seen that the output signal of an eddy current probe is compensated to substantially eliminate the effect of probe lift-off. The compensation is achieved by means of a compensation circuit that is coupled to the probe energizing source and to the probe secondary winding, or windings, to add to the induced voltage a voltage of predetermined magnitude and phase which, in effect, translates without rotation the plot of the complex locus of the signal as a function of lift-off to a position so that a phasor from the origin to operating points on the plot have substantially the same phase angle.

In its broader aspects, this invention is not limited to the specific embodiments illustrated and described. Various changes and modifications may be made without departing from the inventive principles herein disclosed. For example, the turns ratio of the primary and secondary windings may be varied along with other compensation means such as those illustrated in the accompanying drawings. Furthermore, different coil arrangements and combinations may be employed in the probe.

What is claimed is:

1. A method for compensating the output signal of an eddy current probe that is inspecting a steel specimen to minimize the influence of probe lift-off on the phase of the probe output signal, comprising the steps
    exciting an eddy current probe input means with an exciting signal of a given frequency,
    coupling the probe output signal to apparatus for indicating the complex locus of said output signal on an X-Y coordinate system,
    removing the probe from the influence of the specimen and from other undesirable signal influencing means,
    adjusting the electrical and/or magnetic parameters of the probe to move the indication of the probe output signal to the origin of the coordinate system,
    providing an indication of the complex locus of the probe output signal as a function of the change of position of the probe from said removed location to an inspecting location adjacent the surface of the specimen,
    repeating the step immediately-above with at least a second specimen that has metallurgical characteristics that differ from said first-named specimen,
        the indications of the complex loci having substantially linear portions at locations removed from the origin of the coordinate system,
    extending construction lines from said linear portions of the indications to an intersection point where said construction lines intersect,
    determining the distance and direction from the intersection point to said origin,
    establishing the location of a translated origin that is on a straight line through the origin from the intersection point and at the same distance but opposite direction from the origin as the intersection point,
    coupling a signal at the frequency of said exciting signal through a compensating means that is connected to output means of the probe, thereby to produce a compensating signal,
    removing the probe from influence by the specimens and other undesirable signal influencing means,
    adjusting the electrical and/or magnetic parameters of the compensating means to move the origin of the indication of the complex locus of the probe output signal while at the removed location to said translated origin, and
    inspecting a metallic specimen with said probe as compensated above.

2. A method for compensating the output signal of an eddy current probe that is to nondestructively inspect a steel object to minimize the influence of probe lift-off on the phase of the probe output signal, comprising the steps
    exciting an input winding of an eddy current probe with an exciting signal of a given frequency,
    inductively coupling said exciting signal from the input winding to series opposed output windings that are wound on the same coil bobbin as the exciting windings of the probe,
    generating in response to said exciting signal a compensating signal having said given frequency and selectable magnitude and phase, adding said compensating signal with the inductively coupled signal, thereby to produce a probe output signal, selecting the magnitude and phase of said compensating signal to translate, without rotation, the X-Y coordinate plot of the complex locus of a probe output signal that varies as a function of probe lift-off from the surface of said steel object to a location in the coordinate system where phasors from the original origin of the coordinate system to different points on the translated plot that correspond to operating conditions are at substantially the same phase angle.

3. The method claimed in claim 2 wherein the steel being nondestructively inspected is from a group of grades that includes N-80 and P-110.

4. Means for compensating the output of an eddy current probe to be used for nondestructively inspecting a steel object to minimize the influence on the phase of the probe output signal of probe lift-off from the surface of the object, comprising the combination an eddy current probe having a two section coil bobbin with respective primary windings wound in each section and respective secondary windings wound coaxially over a primary winding in each section, said primary windings being wound in series aiding relationship and the secondary windings being wound in series opposed relationship, an adjustable magnetic core disposed in said coil bobbin, a source of exciting signals coupled to said primary windings, probe output means coupled to one end of the series connected secondary windings, an electrical compensating circuit coupled at one end between said source and said primary windings and having other connections to said series connected secondary windings and to said probe output means, means for varying the electrical parameters of the compensating circuit and/or the adjustment of the magnetic core to provide a compensating signal of selectable magnitude and phase, said compensating circuit and magnetic core being adjusted to cause the origin of the complex locus of the probe output signal corresponding to intended operating conditions to translate, substantially without rotation of the complex locus, from its position at the origin of the X-Y coordinate plot made in the absence of said steel object to a new position where phasors from the original origin to different points on the complex locus for a given steel are at substantially the same phase angle.

5. The combination claimed in claim 4 wherein said compensating circuit includes a phase shifting means in series with resistance means.

6. The combination claimed in claim 5 wherein said phase shifting means is a capacitor.

7. The combination claimed in claim 5 wherein said resistance means includes first and second potentiometers having sliding contacts, the sliding contact of the second one of said potentiometers being connected to the other end of said secondary windings.

* * * * *